US009919295B2

(12) United States Patent
Choi et al.

(10) Patent No.: US 9,919,295 B2
(45) Date of Patent: Mar. 20, 2018

(54) HIGH-PERFORMANCE POLYOXOMETALATE CATALYST AND METHOD OF PREPARING THE SAME

(71) Applicant: LG CHEM, LTD., Seoul (KR)

(72) Inventors: Byung Yul Choi, Daejeon (KR); Hyun Jong Shin, Daejeon (KR); Young Hyun Choe, Daejeon (KR); Duk Ki Kim, Daejeon (KR); Hyun Sub Lim, Daejeon (KR); Hyo Sang You, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/502,036

(22) PCT Filed: Jun. 24, 2016

(86) PCT No.: PCT/KR2016/006785
§ 371 (c)(1),
(2) Date: Feb. 6, 2017

(87) PCT Pub. No.: WO2017/026649
PCT Pub. Date: Feb. 16, 2017

(65) Prior Publication Data
US 2017/0225154 A1    Aug. 10, 2017

(30) Foreign Application Priority Data

Aug. 11, 2015  (KR) .................. 10-2015-0113111

(51) Int. Cl.
| | | |
|---|---|---|
| *B01J 27/199* | (2006.01) |
| *B01J 27/14* | (2006.01) |
| *B01J 27/057* | (2006.01) |
| *B01J 23/755* | (2006.01) |
| *B01J 23/75* | (2006.01) |
| *B01J 23/745* | (2006.01) |
| *B01J 23/72* | (2006.01) |
| *B01J 23/50* | (2006.01) |
| *B01J 23/46* | (2006.01) |
| *B01J 23/34* | (2006.01) |
| *B01J 23/30* | (2006.01) |
| *B01J 23/28* | (2006.01) |
| *B01J 23/26* | (2006.01) |
| *B01J 23/22* | (2006.01) |
| *B01J 23/20* | (2006.01) |
| *B01J 23/18* | (2006.01) |
| *B01J 23/14* | (2006.01) |
| *B01J 23/10* | (2006.01) |
| *B01J 23/04* | (2006.01) |
| *B01J 23/02* | (2006.01) |
| *B01J 21/10* | (2006.01) |
| *B01J 21/06* | (2006.01) |
| *B01J 21/02* | (2006.01) |

(52) U.S. Cl.
CPC ............. *B01J 27/199* (2013.01); *B01J 21/02* (2013.01); *B01J 21/06* (2013.01); *B01J 21/063* (2013.01); *B01J 21/066* (2013.01); *B01J 21/10* (2013.01); *B01J 23/02* (2013.01); *B01J 23/04* (2013.01); *B01J 23/10* (2013.01); *B01J 23/14* (2013.01); *B01J 23/18* (2013.01); *B01J 23/20* (2013.01); *B01J 23/22* (2013.01); *B01J 23/26* (2013.01); *B01J 23/28* (2013.01); *B01J 23/30* (2013.01); *B01J 23/34* (2013.01); *B01J 23/464* (2013.01); *B01J 23/50* (2013.01); *B01J 23/72* (2013.01); *B01J 23/745* (2013.01); *B01J 23/75* (2013.01); *B01J 23/755* (2013.01); *B01J 27/0576* (2013.01); *B01J 27/14* (2013.01)

(58) Field of Classification Search
CPC . B01J 27/199; B01J 21/02; B01J 21/06; B01J 21/063; B01J 21/066; B01J 21/10; B01J 23/02; B01J 23/04; B01J 23/10; B01J 23/14; B01J 23/18; B01J 23/20; B01J 23/22; B01J 23/26; B01J 23/28; B01J 23/30; B01J 23/34; B01J 23/464; B01J 23/50; B01J 23/72; B01J 23/745; B01J 23/75; B01J 23/755; B01J 27/0576; B01J 27/14; B01J 37/04; B01J 37/08
USPC ........ 502/209–211, 213, 305–306, 308–319, 502/321
See application file for complete search history.

(56) References Cited

U.S. PATENT DOCUMENTS

| | | | | |
|---|---|---|---|---|
| 4,042,625 A | * | 8/1977 | Matsuzawa ............. | B01J 23/28 502/209 |
| 4,212,767 A | * | 7/1980 | Daniel .................... | B01J 23/24 502/211 |
| 4,414,412 A | * | 11/1983 | DeAlberti ................ | B01J 23/30 502/203 |

(Continued)

FOREIGN PATENT DOCUMENTS

| | | |
|---|---|---|
| JP | 5448331 B2 | 3/2014 |
| JP | 2015-505713 A | 2/2015 |

(Continued)

*Primary Examiner* — Patricia L. Hailey
(74) *Attorney, Agent, or Firm* — Dentons US LLP

(57) ABSTRACT

The present invention relates to a high-performance polyoxometalate catalyst and a method of preparing the same. More particularly, the present invention provides a high-performance polyoxometalate catalyst, the activity and selectivity of which may be improved by controlling the content of vanadium and the like and which has superior reproducibility and may unsaturated carboxylic acid from unsaturated aldehyde in a high yield for a long time, a method of preparing the same, and the like.

18 Claims, No Drawings

(56) References Cited

U.S. PATENT DOCUMENTS

| | | | | |
|---|---|---|---|---|
| 4,804,778 | A * | 2/1989 | Oh-Kita | B01J 23/002 |
| | | | | 502/206 |
| 5,442,108 | A * | 8/1995 | Kawajiri | B01J 23/94 |
| | | | | 562/532 |
| 6,043,184 | A * | 3/2000 | Karmakar | B01J 23/002 |
| | | | | 502/208 |
| 6,060,419 | A * | 5/2000 | Wijesekera | B01J 23/002 |
| | | | | 502/208 |
| 6,387,841 | B1 * | 5/2002 | Devlin | B01J 23/002 |
| | | | | 502/208 |
| 6,444,845 | B1 * | 9/2002 | Karim | B01J 23/002 |
| | | | | 562/534 |
| 6,881,702 | B2 * | 4/2005 | Arnold | B01J 6/004 |
| | | | | 502/212 |
| 6,914,029 | B2 * | 7/2005 | Davis | B01J 27/186 |
| | | | | 502/150 |
| 8,669,201 | B2 | 3/2014 | Nagaki et al. | |
| 9,321,973 | B2 * | 4/2016 | Marchand | B01J 27/186 |
| 2011/0137078 | A1 * | 6/2011 | Nakahara | B01J 23/002 |
| | | | | 562/532 |
| 2011/0237753 | A1 * | 9/2011 | Brazdil | C07C 253/26 |
| | | | | 525/378 |
| 2016/0175818 | A1 * | 6/2016 | Choi | B01J 23/8885 |
| | | | | 562/534 |

FOREIGN PATENT DOCUMENTS

| | | |
|---|---|---|
| JP | 2015-520745 A | 7/2015 |
| KR | 10-0764758 B1 | 10/2007 |

\* cited by examiner

HIGH-PERFORMANCE POLYOXOMETALATE CATALYST AND METHOD OF PREPARING THE SAME

CROSS-REFERENCE TO RELATED APPLICATION(S)

This application is a National Stage Entry of International Application No. PCT/KR2016/006785, filed Jun. 24, 2016, and claims the benefit of and priority to Korean Application No. KR 10-2015-0113111, filed on Aug. 11, 2015, all of which are hereby incorporated by reference in their entirety for all purposes as if fully set forth herein.

TECHNICAL FIELD

The present invention relates to a polyoxometalate catalyst and a method of preparing the same, and more particularly to a catalyst used to produce unsaturated carboxylic acid from unsaturated aldehyde gas by vapor-phase partial oxidation in a shell-and-tube heat exchanger and a method of preparing the same.

BACKGROUND ART

A process of preparing unsaturated fatty acids, via unsaturated aldehydes, from olefin is a representative example of catalytic vapor-phase oxidation.

In partial oxidation of olefin, molybdenum oxide, and transition metal oxide are used to prepare a catalyst. As representative processes, there are a process of producing (meth)acrylic acid, via methacrolein, by oxidizing propylene or isobutylene, a process of producing phthalic anhydride by oxidizing naphthalene or ortho-xylene, and a process of preparing maleic anhydride by partially oxidizing benzene, butylene or butadiene In the first step, propylene or isobutylene is oxidized by oxygen, diluted inert gas, water vapor, and a predetermined amount of catalyst, thereby mainly producing methacrolein. In step 2, the methacrolein is oxidized by oxygen, diluted inert gas, water vapor and a predetermined amount of a catalyst, thereby producing (meth)acrylic acid. A reactor used for such processes may be configured to perform both processes in one apparatus, or to perform each of the processes in a different apparatus.

(Meth)acrylic acid, which is reacted with alcohol, is mainly used to prepare (meth)acrylate used as a coating agent for paint, textile assistants, and paper. High-purity (meth)acrylic acid is used as a raw material for highly hygroscopic resins, demand for which has rapidly increased in recent years.

In general, a metal oxide catalyst is produced by coprecipitation reaction, hydrothermal synthesis, sol-gel synthesis, physical mixing reaction, etc. In such reaction processes, the metal oxide catalyst is precipitated in a polyanion, metal oxide, or metal hydroxylate form. Here, the physical properties and morphology of a precipitate are changed depending upon the pH, concentration, reaction temperature, and aging time of an aqueous solution, whereby the physical state, particle size, and crystal structure of the metal oxide catalyst are affected.

As examples of ligands bound to oxo anions and transition metal precursors which are used in catalysts for producing unsaturated fatty acid, there are —$NH_4$, —$NH2$, —$NOx$, —Cl, —F, —N, —OH (hydroxyl), —$SOx$, —CO, —COO, —$C_nH_mO_x$, alkoxide (O-Metal), and the like. Such ligands, which are essential ingredients for dissolving or purifying metal oxide, may be utilized as factors for changing physicochemical characteristics of a catalyst according to a suitable control method and thus controlling the activity of the catalyst.

In the related art, "Technology for Preparing Catalyst" introduced in Japanese Patent No. 4295521, a catalyst is prepared by powder-coating and firing a massive carrier. Here, the prepared catalyst is an acrylic catalyst characterized in that a mass reduction rate of a dried product thereof is 5 to 40% by mass at a catalyst drying temperature of 300° C. in an air atmosphere. However, such a preparation method causes structural change of the catalyst due to a relatively high drying temperature, thereby negatively affecting the performance of the catalyst and thus a conversion rate tends to be poor.

In addition, KR 10-0746971 B1 introduces a catalyst, which includes molybdenum and vanadium, and a catalyst poison in a content of 10 to 100 ppb measured by ion chromatography, further includes at least one volatile catalyst poison ingredient, and generates acrylic acid by catalytic vapor-phase oxidation between oxygen and acrolein, and a method of preparing acrylic acid, which includes a step of performing contact vapor-phase oxidation between oxygen and acrolein using the catalyst.

The catalyst, which is prepared by artificially adding a catalyst poison ingredient, i.e., aqueous ammonia, can lower hot spot temperature and inhibit reaction efficiency reduction accompanied by deterioration, thereby highly, stably maintaining an acrolein conversion rate for a long time. However, when a reducing substance, such as ammonia, is present in the catalyst, the reducing substance acts as a catalyst poison, thereby greatly increasing reaction temperature and, after a long period of operation, activating the catalyst. Accordingly, although the reducing substance can be used as a catalyst poison for controlling catalytic activity, there is considerable difficulty in quantitatively controlling the amount of the reducing substance in a process of producing the catalyst.

Meanwhile, treatment with an inorganic salt present in a catalyst precursor should be performed to be decreased during a process of preparing a catalyst. However, such an inorganic salt is additionally added, and thus, there is a disadvantage in that a process of removing the reducing substance is additionally required. Accordingly, there is a need for a technology for simply controlling, through sublimation, a type of ligands included in a catalyst and the amount thereof, when the catalyst is calcined, while providing superior reproducibility.

DISCLOSURE

Technical Problem

Therefore, the present invention has been made in view of the above problems, and it is one object of the present invention to provide a high-performance polyoxometalate catalyst which may control activity and selectivity, has superior reproducibility, may produce unsaturated carboxylic acid from unsaturated aldehyde in a high yield for a long time, a method of preparing the same, and the like.

The above and other objects can be accomplished by the present invention described below.

Technical Solution

In accordance with the present invention, the above and other objects can be accomplished by the provision of a polyoxometalate catalyst, including a metal oxide represented by Formula 1 below:

$$MO_aA_bV_cB_dC_eD_fO_g,$$ [Formula 1]

wherein A is one or more elements selected from the group consisting of W and Cr; B is one or more elements selected from the group consisting of P, As, B, Sb, Ce, Pb, Mn, Nb and Te; C is one or more elements selected from the group consisting of Si, Al, Zr, Rh, Cu, Ni, Ti, Ag, Fe, Co and Sn; D is one or more selected from the group consisting of Na, K, Li, Rb, Cs, Ta, Ca, Mg, Sr and Ba; and a, b, c, d, e, f, and g represent atomic ratios of the respective elements, wherein, when a=12, b is 0.01 to 15; c is 0.01 to 15, d is 0 to 20, e is 0 to 20, f is 0 to 20; and g is determined depending upon oxidation states of the respective ingredients, and wherein a mole ratio of V to A (V/A) is 0.01 to 10.

Each of d, e and f may be, for example, 0.01 to 20.

The vanadium (V) may include, for example, 30% or more of vanadium having an oxidation number of 4+.

The polyoxometalate catalyst may include, for example, an inert carrier, as a supporter of the metal oxide.

A loading amount of a metal oxide coated on the inert carrier may be, for example, 30 to 80% by weight.

The polyoxometalate catalyst may be, for example, a catalyst for vapor-phase partial oxidation to produce unsaturated carboxylic acid from unsaturated aldehyde.

In accordance with another aspect of the present invention, there is provided a method of preparing the polyoxometalate catalyst according to claim 1, the method including: (A) a step of preparing a suspension including metal precursors to produce a metal oxide represented by Formula 1 and, as needed, adjusting pH to 0 to 7.5 by adding an acid, followed by increasing a viscosity by means of a homogenizer to form polyoxometalate; (B) a step of loading 20 to 50% by weight of the formed polyoxometalate to an inert carrier to prepare a loaded substance; (C) a step of drying the loaded substance to obtain a loaded substance having a ligand sublimation rate of 0% or more calculated by Equation 1 below; and (D) a step of firing the dried loaded substance to obtain a polyoxometalate catalyst:

Ligand sublimation rate (%)=(mass of sublimated ligand/mass of ligand before sublimation)×100. [Equation 1]

A vanadium (V) precursor represented by Formula 1 may be, for example, a compound containing vanadium with an oxidation number of 4+.

The compound containing vanadium with oxidation number of 4+ may be, for example, a vanadyl-containing compound.

In step (A), the polyoxometalate may have, for example, a viscosity of 1,000 to 15,000 cps or 3,000 to 8,000 cps.

The polyoxometalate formed in step (A) may be, for example, dried and then filtered and dried, followed by pulverization.

The loading of step (B) may be carried out, for example, by spraying the polyoxometalate onto the inert carrier or spraying the polyoxometalate along with water onto the inert carrier.

A ligand of the metal precursor may be one or more selected from, for example, —NH$_4$, —NH$_2$, —NOx, where x is an integer of 1 to 4, —Cl, —F, —N, —OH, —Sox, wherein x is an integer of 1 to 4, —CO, —COO, —SCN, —CN, —NCS, —ONO, —NC, —CnHmOx, where n is an integer of 1 to 20, m is an integer of 1 to 40 and x is an integer of 1 to 10, and C$_1$ to C$_{20}$ alkoxide.

In step (A), the concentration of the suspension may be 25 to 45% by weight or 30 to 40% by weight.

The drying of step (C) may be, for example, hot air drying.

The loading of step (B) may be carried out, for example, by repeating a process of coating the inert carrier with the polyoxometalate and drying the coated inert carrier once or more.

The drying of step (C) may be carried out, for example, at 100 to 230° C.

In step (A), the viscosity of the suspension may be increased, for example, by means of a homogenizer at 25 to 50° C., thereby forming polyoxometalate.

The firing of step (D) may be performed, for example, at 350 to 500° C. for 1 to 10 hr.

In accordance with yet another aspect of the present invention, there is provided a method of preparing unsaturated carboxylic acid, wherein vapor-phase partial oxidation to produce the unsaturated carboxylic acid from unsaturated aldehyde gas is carried out at 240 to 450° C. under 0.1 to 10 atm in a fixed-bed catalytic reactor filled with the polyoxometalate catalyst.

The fixed-bed catalytic reactor may be, for example, a shell-and-tube heat exchanger.

Advantageous Effects

As apparent from the above description, the present invention provides a high-performance polyoxometalate catalyst, the activity and selectivity of which may be improved by controlling the content of vanadium and the like and which has superior reproducibility and may unsaturated carboxylic acid from unsaturated aldehyde in a high yield for a long time, a method of preparing the same, and the like.

BEST MODE

Hereinafter, the present invention is described in more detail.

A polyoxometalate catalyst of the present invention includes a metal oxide represented by Formula 1 below:

$$MO_aA_bV_cB_dC_eD_fO_g,$$ [Formula 1]

wherein A is one or more elements selected from the group consisting of W and Cr; B is one or more elements selected from the group consisting of P, As, B, Sb, Ce, Pb, Mn, Nb and Te; C is one or more elements selected from the group consisting of Si, Al, Zr, Rh, Cu, Ni, Ti, Ag, Fe, Co and Sn; D is one or more selected from the group consisting of Na, K, Li, Rb, Cs, Ta, Ca, Mg, Sr and Ba; and a, b, c, d, e, f, and g represent atomic ratios of the respective elements, wherein, when a=12, b is 0.01 to 15; c is 0.01 to 15, d is 0 to 20, e is 0 to 20, f is 0 to 20; and g is determined depending upon oxidation states of the respective ingredients, and wherein a mole ratio of V to A (V/A) is 0.01 to 10.

In the present disclosure, the term "polyoxometalate" has a generally defined meaning, unless specified otherwise.

In the present disclosure, the term "ligand" refers to a group of anions bound to metal cations in a metal precursor, and has a generally defined meaning unless specified otherwise.

In another embodiment, a mole ratio of V to A may be 0.05 to 5, preferably 0.5 to 4, more preferably 0.5 to 3. Within this range, an oxidation state of vanadium is affected, whereby the catalyst has superior activity and selectivity. In particular, tungsten (W) functions as a structural promoter in the catalyst and thus increases the amount of $V^{4+}$ in the catalyst, thereby increasing catalytic activity.

The vanadium (V) may include, for example, 30 (mol) % or more, 40% or more, or 50% or more of vanadium with an oxidation number of 4+. Within this range, activity and selectivity of the catalyst are increased, superior reproducibility is exhibited, and unsaturated carboxylic acid may be produced in a high yield for a long time.

In the metal oxide, a mole ratio of $V^{4+}$ to a total content of vanadium (V) ($V^{4+}/(V^{4+}+V^{5+})$) is, for example, 0.3 to 1, 0.4 to 0.8, or 0.5 to 0.8. Within this range, the activity and selectivity of the catalyst are increased, superior reproducibility is provided, and unsaturated carboxylic acid is produced in a high yield for a long time.

b may be, for example, 0.1 to 10, 1.0 to 6.0, or 1.5 to 5.0. Within this range, the activity, selectivity, and lifespan of the catalyst are greatly improved.

c may be, for example, 0.5 to 10, 1.0 to 5.0, or 2.0 to 3.0. Within this range, the activity, selectivity, and lifespan of the catalyst are greatly improved.

Each of d, e, and f may be, for example, 0.01 to 20 or 0.05 to 10.

In another embodiment, d may be 0.01 to 0.5, 0.05 to 0.4, or 0.1 to 0.3, e may be 0.1 to 8.0, 0.5 to 7.0, or 1.0 to 5.5, and f may be 0.1 to 5.0, 0.5 to 2, or 0.8 to 1.3. Within this range, the catalyst exhibits superior activity and selectivity.

A may be, for example, W, B may be, for example, Nb or Mn or a combination thereof, C may be, for example, one or more selected from the group consisting of Cu, Fe, and Co, D may be, for example, Sr. In this case, the activity and selectivity of the catalyst are increased, superior reproducibility is provided, and unsaturated carboxylic acid is produced in a high yield for a long time.

The polyoxometalate catalyst may include, for example, an inert carrier, as a supporter of the metal oxide.

The inert carrier may be one or more selected from the group consisting of, for example, porous aluminosilicate, silicon carbide alumina, and silica.

A loading amount of a metal oxide coated on the inert carrier may be, for example, 30 to 80% by weight, 40 to 70% by weight, or 50 to 60% by weight. Within this range, the catalyst has superior activity and selectivity.

The polyoxometalate catalyst may be, for example, a catalyst for vapor-phase partial oxidation to produce unsaturated carboxylic acid from unsaturated aldehyde.

A method of preparing polyoxometalate catalyst of the present invention includes (A) a step of preparing a suspension including metal precursors to produce a metal oxide represented by Formula 1 and, as needed, adjusting pH to 0 to 7.5 by adding an acid, followed by increasing a viscosity by means of a homogenizer to form polyoxometalate; (B) a step of loading 20 to 50% by weight of the formed polyoxometalate to an inert carrier to prepare a loaded substance; (C) a step of drying the loaded substance to obtain a loaded substance having a ligand sublimation rate of 0% or more calculated by Equation 1 below; and (D) a step of firing the dried loaded substance to obtain a polyoxometalate catalyst:

Ligand sublimation rate (%)=(mass of sublimated ligand/mass of ligand before sublimation)×100. [Equation 1]

A vanadium (V) precursor represented by Formula 1 may be, for example, a compound containing vanadium with an oxidation number of 4+, preferably a vanadyl-containing compound. Within this range, the activity and selectivity of the catalyst are increased, superior reproducibility is provided, and unsaturated carboxylic acid is produced in a high yield for a long time.

The vanadyl-containing compound may be, for example, vanadyl acetylacetonate, vanadyl sulfate, or the like.

In step (A), the polyoxometalate may have, for example, a viscosity of 1,000 to 15,000 cps or 3,000 to 8,000 cps. Within this range, the catalyst exhibits superior activity and selectivity.

The pH adjusted in step (A) may be, for example, 3 to 5, preferably 4 to 5. Within this range, the catalyst exhibits superior activity, selectivity, and lifespan and a drying time and temperature are decreased.

The polyoxometalate formed in step (A) may be, for example, dried and then filtered and dried, followed by being pulverization.

The filter may be used, for example, to remove inorganic salts from slurry-type polyoxometalate through a filter and/or a filter press.

A ligand of the metal precursor may be one or more selected from, for example, $-NH_4$, $-NH_2$, $-NOx$, where x is an integer of 1 to 3, $-Cl$, $-F$, $-N$, $-OH$, $-Sox$, wherein x is an integer of 3 to 4, $-CO$, $-COO$, $-SCN$, $-CN$, $-NCS$, $-ONO$, $-NC$, $-CnHmOx$, where n is an integer of 1 to 20, m is an integer of 1 to 40 and x is an integer of 1 to 10, and $C_1$ to $C_{20}$ alkoxide. In this case, the oxidation states and morphologies of the transition metal and transition metal oxide are affected, thereby improving the activity and selectivity of the catalyst.

In step (A), the concentration of the suspension may be 25 to 45% by weight or 30 to 40% by weight. Within this range, the catalyst exhibits superior activity and selectivity.

In an embodiment, in step (A), the viscosity of the suspension is increased at 25 to 50° C., preferably 20 to 40° C., by means of a homogenizer, thereby forming polyoxometalate. Within this range, the catalyst exhibits superior activity and selectivity. Here, the polyoxometalate may correspond to a precursor of the polyoxometalate catalyst of the present disclosure.

The viscosity of the polyoxometalate may be, for example, 1,000 to 15,000 cps or 3,000 to 8,000 cps. Within this range, the catalyst exhibits superior activity and selectivity.

The polyoxometalate of step (A) may further include, for example, a surfactant. In this case, a layer separation phenomenon in a coprecipitated solution may be alleviated.

The surfactant may be, for example, a nonionic or neutral surfactant.

The nonionic surfactant may be, for example, $CH_3(CH_2)_{15}(EO)_nOH$, where n is an integer of 2 to 20.

The neutral surfactant may be, for example, $CH_3(CH_2)_{n-1}NH_2$, wherein n is an integer of 12 to 16.

The surfactant may be included, for example, in an amount of 0.1% by weight or less, 0.001 to 0.1% by weight, or 0.01 to 0.05% by weight based on a total weight of a slurry solution. Within this range, a layer separation phenomenon in a coprecipitated solution may be alleviated.

In step (A), the method of forming polyoxometalate may be a general polyoxometalate formation method, such as hydrothermal reaction, coprecipitation, or the like, without any specific limitation, unless specified otherwise.

The coating of the step (B) may be carried out, for example, by spraying polyoxometalate onto the inert carrier or spraying polyoxometalate along with water onto the inert carrier.

The spraying with polyoxometalate may be carried out, for example, by spraying slurry-type polyoxometalate, which has not been filtered or dried, onto the inert carrier using a nozzle to coat the slurry-type polyoxometalate on the inert carrier.

The spraying with polyoxometalate and water may be carried out, for example, by spraying polyoxometalate, which has been filtered and/or dried, along with water onto the inert carrier to coat the slurry-type polyoxometalate on the inert carrier.

In the loaded substance of step (B), the loading amount of polyoxometalate calculated by Equation 2 below may be, for example, 15 to 50%, 20 to 50%, 20 to 40%, or 20 to % Within this range, the catalyst exhibits superior activity and selectivity.

Loading amount (%)=(total mass of catalyst precursors/total mass of loaded substance)×100   [Equation 2]

The loading of step (B) may be carried out, for example, by repeating a process of coating polyoxometalate onto the inert carrier and drying the coated polyoxometalate once or more, once to ten times, once to eight times, or five times to eight times. Within this range, the catalyst exhibits superior activity and selectivity.

The drying of step (C) may be, for example, hot air drying.

The drying may be carried out, for example, in a silicon carbide (SiC) container, an alumina container, a stainless steel container, a metal container, or a container made of an incombustible material having heat transfer ability.

The drying of step (C) may be carried out, for example, at 100 to 230° C., 110 to 200° C., or 120 to 150° C. for 3 to 10 hours or 5 to 8 hours.

The ligand sublimation rate of step (C) may be, for example, 1.7% or more, or 1.7 to 4%. Within this range, the activity, selectivity, and lifespan of the catalyst are greatly improved.

The firing of step (D) may be performed, for example, at 350 to 550° C. or 400 to 500° C. for 1 to 10 hours or 3 to 5 hours.

In steps (A) to step (D), a total weight reduction rate (%) calculated by Equation 3 below may be, for example, 30 to 50%, 35 to 45%, or 40 to 45%. Within this range, the catalyst exhibits superior activity and selectivity:

$T$ total weight reduction rate (%)=(mass of removed materials/mass of a total of added materials including a solvent)×100   [Equation 3]

In steps (A) to (D), the total ligand sublimation rate (%) calculated by Equation 4 below may be, for example, 0.1 to 20%, 1 to 10%, or 2 to 5%. Within this range, the catalyst exhibits superior activity and selectivity:

Total ligand sublimation rate (%)=(mass of removed ligand/mass of a total of added materials including a solvent)×100   [Equation 4]

The polyoxometalate catalyst may have, for example, a cylindrical shape, a hollow cylindrical shape), or a spherical shape.

An external diameter of the polyoxometalate catalyst may be, for example, 3 to 10 mm, or 5 to 8 mm.

A ratio of the length to the diameter (external diameter) (L/D) of the cylinder type catalyst may be, for example, 1 or less, 0.1 to 1, or 1.0 to 1.3.

A method of preparing the unsaturated carboxylic acid of the present invention is characterized in that vapor-phase partial oxidation to produce unsaturated carboxylic acid from unsaturated aldehyde gas is carried out at 240 to 450° C. under 0.1 to 10 atm in a fixed-bed catalytic reactor filled with the polyoxometalate catalyst.

The unsaturated aldehyde may be, for example, methacrolein.

The unsaturated carboxylic acid may be, for example, unsaturated fatty acid. In another embodiment, the unsaturated carboxylic acid may be (meth)acrylic acid or the like.

The fixed-bed catalytic reactor may be, for example, a fixed-bed catalytic reactor filled with a catalyst using a method by which an occupation volume of the catalyst is decreased.

The unsaturated aldehyde gas may be added, for example, along with unsaturated fatty acid.

The vapor-phase partial oxidation may be carried out, for example, at 240 to 370° C. and 0.4 to 3 atm. In another embodiment, the vapor-phase partial oxidation may be carried out at 250 to 310° C. and 1 to 3 atm.

The vapor-phase partial oxidation may be carried out, for example, by introducing unsaturated aldehyde at a space velocity of 80 to 100 hr$^{-1}$, 20% by volume or less of oxygen (not including 0% by volume), 50% by volume or less of water vapor (not including 0% by volume), and 20 to 80% by volume or less of an inert gas into the reactor.

In another embodiment, the vapor-phase partial oxidation may be carried out by introducing a raw material gas, which includes unsaturated aldehyde, oxygen, steam, and nitrogen, at a space velocity of 500 to 3000 hr$^{-1}$ (STP), into the reactor.

The fixed-bed catalytic reactor may be, for example, a shell-and-tube heat exchanger.

A material of the shell-and-tube heat exchanger may be, for example, silicon carbide (SiC), stainless steel, a metal, or a material having superior heat transfer ability.

The aforementioned description is provided only to illustrate embodiments according to the present invention. Those skilled in the art will appreciate that various modifications, additions and substitutions are possible, without departing from the scope and spirit of the invention. Therefore, it is obvious that the modifications, additions and substitutions are included in the scope of the present invention.

Example 1

246 g of ammonium tungstate, 1,000 g of ammonium molybdate, and 12 g of niobium oxalate (NbC$_2$O$_4$) were added while stirring 3000 ml of distilled water at 100° C., thereby preparing a solution (1) composed of Mo, A, and B ingredients of Formula 1. Separately, 276 g of vanadyl sulfate was dissolved in 1000 ml of distilled water, thereby preparing the solution (2).

The solution (1) was mixed with the solution (2), and then 570 g of Cu(CH$_3$COO)$_2$.H$_2$O, 99 g of strontium nitrate, 23 g of manganese nitrate, and 95 g of iron nitrate, as C and D ingredients of Formula 1, were added thereto, thereby preparing a suspension. The pH of the suspension was adjusted to 4 to 5 using dilute sulfuric acid, and then a homogenizer was operated until polyoxometalate formed a slurry in which viscosity was sufficiently increased.

Subsequently, the slurry-type polyoxometalate was coated on a spherical carrier, aluminosilicate (Saint Gobain, SA5218) with an external diameter of 4.0 mm to 8.0 mm, by means of a spray nozzle and was sufficiently dried at 120° C. This process was repeated eight times. As a result, a loaded substance loaded in an amount of 25% by weight was prepared.

Subsequently, the loaded substance was fired at 500° C. for five hours or more, thereby preparing a spherical polyoxometalate catalyst with a final external diameter of 4.7 mm, 5.4 mm, or 7.8 mm which was slightly larger, particularly 0.2 to 0.4 mm larger, than the external diameter of the carrier. In this case, the compositions of elements, except for oxygen, of a generated polyoxometalate catalyst are as follows:

$$Mo_{12}V_{5.0}W_{2.0}Nb_{0.1}Cu_{5.0}Sr1.0Mn_{0.2}Fe_{0.5}$$

Example 2

A polyoxometalate catalyst was prepared in the same manner as in Example 1, except that ammonium tungstate was used in an amount of 123 g. The compositions of elements, except for oxygen, of a generated catalyst ingredient are as follows:

$Mo_{12}V_{5.0}W_{5.0}Nb_{0.1}Cu_{5.0}Sr_{1.0}Mn_{0.2}Fe_{0.5}$

Comparative Examples 1

A polyoxometalate catalyst was prepared in the same manner as in Example 1, except that vanadyl sulfate was not used. The compositions of elements, except for oxygen, of a generated catalyst ingredient are as follows:

$Mo_{12}W_{5.0}Nb_{0.1}Cu_{5.0}Sr_{1.0}Mn_{0.2}Fe_{0.5}$

Comparative Examples 2

A polyoxometalate catalyst was prepared in the same manner as in Example 1, except that ammonium tungstate was not used. The compositions of elements, except for oxygen, of a generated catalyst ingredient are as follows:

$Mo_{12}V_{5.0}Nb_{0.1}Cu_{5.0}Sr_{1.0}Mn_{0.2}Fe_{0.5}$

Reference Example 1

A polyoxometalate catalyst was prepared in the same manner as in Example 1, except that ammonium vanadate was used instead of vanadyl sulfate. The compositions of elements, except for oxygen, of a generated catalyst ingredient are as follows:

$Mo_{12}V_{5.0}W_{2.0}Nb_{0.1}Cu_{5.0}Sr1.0Mn_{0.2}Fe_{0.5}$

Test Example

The properties of the polyoxometalate catalyst prepared according to each of Examples 1 and 2, Comparative Examples 1 and 2, and Reference Example 1 was measured by the following methods. Results are summarized in Table 1 below.

Ratios of $V^{4+}$ and $V^{5+}$: Measured using the prepared catalysts by means of XPS (ESCA) (device name: X-ray photoelectron spectroscopy, model name: UK-Multilab 2000, manufacturer: Thermos VG). Here, vanadium having an oxidation number of 2+ or 3+ was not detected.

Ligand sublimation rate: the mass of sublimated ligand was measured and calculated according to Equation 1 below:

Ligand sublimation rate (%)=(mass of sublimated ligand/mass of ligand before sublimation)×100.  [Equation 1]

Viscosity (cps): Measured by means of a Brookfield viscometer with #63 spindle at 2 RPM and room temperature (resistance: 5 to 6%).

<Catalyst Activity Test>

Using a stainless steel reactor filled with the catalyst, which was obtained according to each of Examples 1 to 2, Comparative Examples 1 and 2, and Reference Example 1, as a fixed bed, aldehyde was introduced with a mixed gas, which was composed of oxygen, water vapor, and an inert gas, at a space velocity of 100 hr$^{-1}$ and 240 to 310° C. under a reaction pressure of 1 to 3 atm, whereby vapor-phase partial oxidation occurred. A conversion rate, selectivity, and yield of the reactant (acrolein) were respectively calculated according to Equations 5 to 7 below. Results are summarized in Table 1 below.

Conversion rate of acrolein (%)=[number of moles of reacted acrolein/number of moles of supplied acrolein]×100  [Equation 5]

Selectivity of acrolein (%)=[number of moles of generated acrylic acid/number of moles of reacted acrolein]×100  [Equation 6]

Yield (%)=[number of moles of generated acrylic acid/number of moles of supplied acrolein]×100  [Equation 7]

TABLE 1

| Classification | Ligand sublimation rate (% by weight) | Mole ratio of V/W | pH of reaction solution | Ratio n of V4+/(V4 + V5+) | Acrolein conversion rate (%) | Acrolein selectivity (%) | Acrylic acid yield (%) |
|---|---|---|---|---|---|---|---|
| Example 1 | 2.8 | 2.5 | 4 to 5 | 0.70 | 97.75 | 96.20 | 93.41 |
| Example 2 | 2.8 | 1 | 4 to 5 | 0.60 | 97.0 | 95.1 | 92.24 |
| Comparative Examples 1 | 2.5 | 0 | 4 to 5 | 0.0 | 60.04 | 80.5 | 48.33 |
| Comparative Examples 2 | 2.8 | ∞ | 4 to 5 | 0.0 | 57.18 | 78.4 | 44.82 |
| Reference Example 1 | 2.8 | 2.5 | 4 to 5 | 0.55 | 97.30 | 95.2 | 92.62 |

As shown in Table 1, it can be confirmed that the polyoxometalate catalysts (Example 1 to 2), in which the V/A value was adjusted, according to the present invention, exhibit superior conversion rate, selectivity, yield, and the like, compared to a conventional technology and Comparative Examples 1 and 2, which were outside the V/A range of the present invention.

In addition, it can be confirmed that, when the $V^{4+}$-containing precursor is used as a vanadium precursor, selectivity and yield considerably increase, compared to the case in which the $V^{5+}$-containing precursor is used.

In addition, it can be confirmed that the ligand sublimation rate, the pH of the suspension, and the like have some effect on catalytic activity, selectivity, and yield.

Further, it can be confirmed that the polyoxometalate catalysts of the present invention (Examples 1 and 2) may be reacted in a broader reaction temperature range, i.e., 250 to 310° C., than a reaction temperature range, i.e., 270 to 310° C., of a conventional technology, and thus, may be reacted for a longer time, compared to the conventional cases.

The invention claimed is:

1. A polyoxometalate catalyst, comprising a metal oxide represented by Formula 1 below:

$$Mo_a A_b V_c B_d C_e D_f O_g,$$ [Formula 1]

wherein A is one or more elements selected from the group consisting of W and Cr; B is one or more elements selected from the group consisting of P, As, B, Sb, Ce, Pb, Mn, Nb and Te; C is one or more elements selected from the group consisting of Si, Al, Zr, Rh, Cu, Ni, Ti, Ag, Fe, Co and Sn; D is one or more selected from the group consisting of Na, K, Li, Rb, Cs, Ta, Ca, Mg, Sr and Ba; and a, b, c, d, e, f, and g represent atomic ratios of the respective elements, wherein, when a=12, b is 0.01 to 15; c is 0.01 to 15, d is 0 to 20, e is 0 to 20, f is 0 to 20; and g is determined depending upon oxidation states of the respective ingredients, wherein a mole ratio of vanadium (V) to A (V/A) is 0.01 to 10, and wherein the vanadium comprises 30 mol % or more of vanadium having an oxidation number of 4+.

2. The polyoxometalate catalyst according to claim 1, wherein each of d, e and f is 0.01 to 20.

3. The polyoxometalate catalyst according to claim 1, wherein the polyoxometalate catalyst comprises an inert carrier, as a supporter of the metal oxide.

4. The polyoxometalate catalyst according to claim 3, wherein a loading amount of a metal oxide coated on the inert carrier is 30 to 80% by weight.

5. The polyoxometalate catalyst according to claim 1, wherein the polyoxometalate catalyst is a catalyst for vapor-phase partial oxidation to produce unsaturated carboxylic acid from unsaturated aldehyde.

6. A method of preparing the polyoxometalate catalyst according to claim 1, the method comprising: (A) a step of preparing a suspension comprising metal precursors to produce a metal oxide represented by Formula 1 and, as needed, adjusting pH to 0 to 7.5 by adding an acid, followed by increasing a viscosity by means of a homogenizer to form polyoxometalate; (B) a step of loading 20 to 50% by weight of the formed polyoxometalate to an inert carrier to prepare a loaded substance; (C) a step of drying the loaded substance to obtain a loaded substance having a ligand sublimation rate of 0% or more calculated by Equation 1 below; and (D) a step of firing the dried loaded substance to obtain a polyoxometalate catalyst:

Ligand sublimation rate (%)=(mass of sublimated ligand/mass of ligand before sublimation)×100 [Equation 1].

7. The method according to claim 6, wherein the compound containing vanadium with oxidation number of 4+ is a vanadyl-containing compound.

8. The method according to claim 6, wherein, in step (A), the polyoxometalate has a viscosity of 5,000 to 20,000 cps.

9. The method according to claim 6, wherein, in step (A), the polyoxometalate is dried and then filtered and dried, followed by pulverization.

10. The method according to claim 6, wherein the loading of step (B) is carried out by spraying the polyoxometalate onto the inert carrier or spraying the polyoxometalate along with water onto the inert carrier.

11. The method according to claim 6, wherein a ligand of the metal precursor is one or more selected from —$NH_4$, —$NH_2$, —$NOx$, where x is an integer of 1 to 3, —Cl, —F, —N, —OH, —$Sox$, wherein x is an integer of 3 to 4, —CO, —COO, —SCN, —CN, —NCS, —ONO, —NC, —$C_nH_mO_x$, where n is an integer of 1 to 20, m is an integer of 1 to 40 and x is an integer of 1 to 10, and $C_1$ to $C_{20}$ alkoxide.

12. The method according to claim 6, wherein, in step (A), a concentration of the suspension is 25 to 45% by weight.

13. The method according to claim 6, wherein the drying of step (C) is hot air drying.

14. The method according to claim 6, wherein the loading of step (B) is carried out by repeating a process of coating the inert carrier with the polyoxometalate and drying the coated inert carrier once or more.

15. The method according to claim 6, wherein the drying of step (C) is carried out at 100 to 230° C.

16. The method according to claim 6, wherein, in step (A), a viscosity of the suspension is increased by means of a homogenizer at 25 to 50° C., thereby forming polyoxometalate.

17. The method according to claim 6, wherein the firing of step (D) is performed at 350 to 550° C. for 1 to 10 hr.

18. A method of preparing unsaturated carboxylic acid, wherein vapor-phase partial oxidation to produce the unsaturated carboxylic acid from unsaturated aldehyde gas is carried out at 240 to 450° C. under 0.1 to 10 atm in a fixed-bed catalytic reactor filled with the polyoxometalate catalyst according to claim 1.

* * * * *